Oct. 8, 1940. L. B. CODDINGTON Plant Pat. 427
ROSE PLANT
Filed May 14, 1940
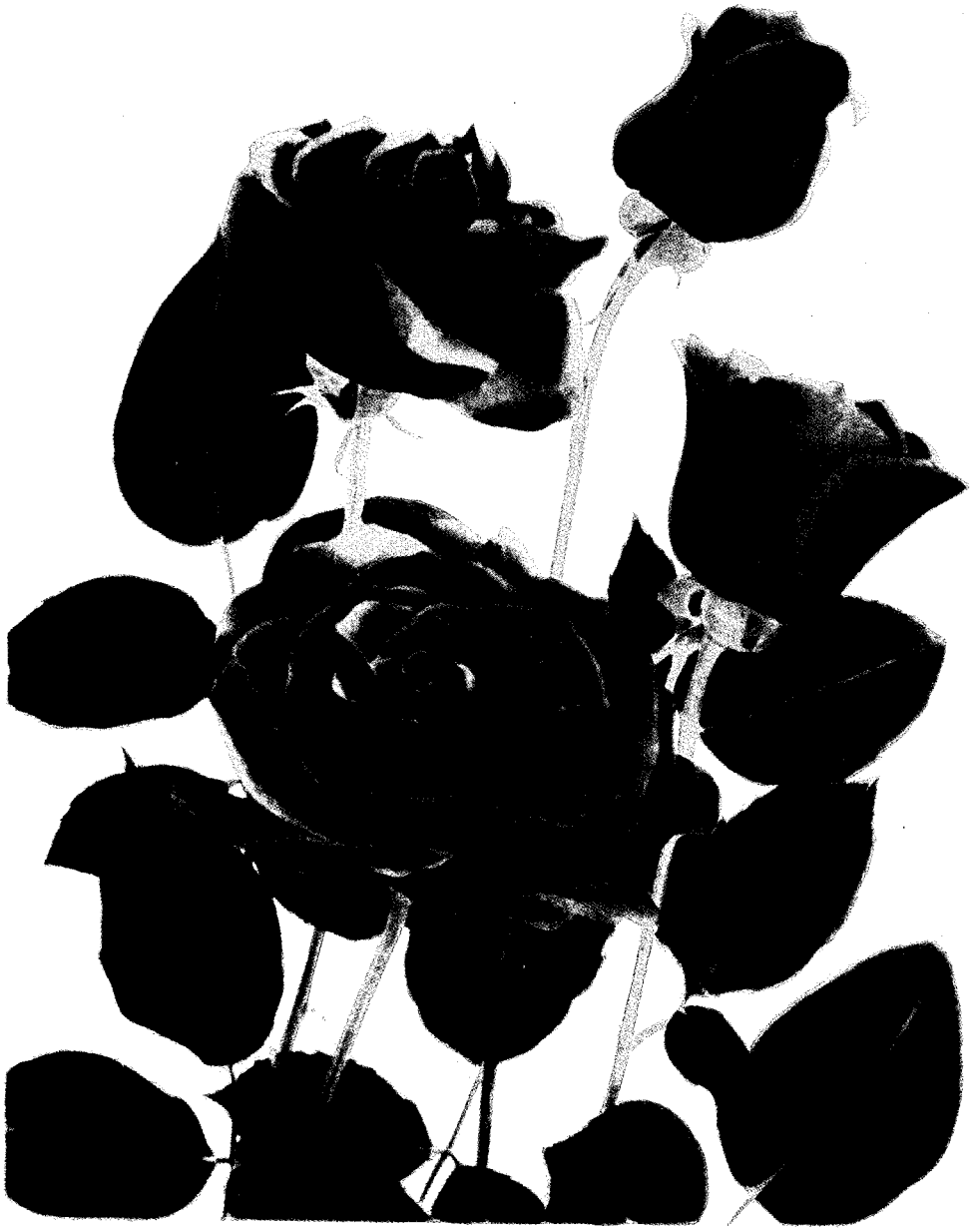
Inventor
L. B. Coddington,
By Robb & Robb
Attorneys Patented Oct. 8, 1940

Plant Pat. 427

UNITED STATES PATENT OFFICE

427

ROSE PLANT

Lyman B. Coddington, Murray Hill, N. J., assignor to L. B. Coddington Co., Murray Hill, N. J., a corporation of New Jersey Application May 14, 1940, Serial No. 335,133

1 Claim. (Cl. 47—61)

The present invention relates to a new and distinct variety of rose plant, the result of a definite effort, by hybridizing certain known varieties, to produce an improved hybrid tea having a number of desirable features.

This new variety I have found to be a good grower, very well branched with an unusual amount of foliage. It is also an excellent bloomer, and an important feature resides in its habit of quickly repeating its bloom the second time after its first bloom. It is also particularly notable that this new variety possesses a high rating for form, color, and fragrance, the rose holding its color far better than most red roses, without turning purple as the bloom ages.

The new variety is particularly useful as a garden rose for decoration purposes.

Other detailed characteristics of novelty and distinctiveness are indicated in the following detailed description of the variety in which the color terminology employed accords with Ridgway's Color Standard:

Type: Half hardy; tall bush; greenhouse and outdoor; seedling; for cut flowers and garden decoration.

Class: Hybrid tea.

Breeding or discovery: Seedling.

*Seed parent.*—(An unnamed seedling Sensation × America).

*Pollen parent.*—E. G. Hill.

*Propagation.*—Holds its distinguishing characteristics through succeeding propagations by cuttings, grafting, and budding.

*Flower*

Locality where grown: Murray Hill, New Jersey.

Flowers borne: Singly on strong, long stems.

Quantity of bloom: Free outdoors and in greenhouse.

Continuity: Continuous.

Fragrance: Moderate, sweet-clover fragrance.

Bud:

*Peduncle.*—Long; heavy; erect; stiff; Oil Green, Plate V; smooth; no hairs or prickles.

*Before calyx breaks.* — *Size* — medium. *Form*—pointed with a conspicuous neck with appendages on the surface of the bud, with slender foliaceous parts extending beyond the tip of the bud equal to ¼ of its length.

*As calyx breaks.*—*Color*—between Ox-Blood and Carmine, Plate I.

*As first petal opens.*—*Size*—medium. *Form*—ovoid. *Color*: outside — Ox-Blood Red and Carmine, Plate I; inside—between Carmine and Spectrum Red, Plate I. *Opening*—opens up well.

Bloom:

*Size, when fully open.*—Medium, four inches to four and one-half inches.

*Petalage.*—Double, from 30 to 35 petals; arranged regularly.

*Form.*—Cupped at first, becoming flat; petals remaining at first loosely cupped, rolled; becoming later, at maturity, loosely rolled outward.

Petals: Leathery; with inside shiny and velvety and outside satiny.

*Shape.*—Outside—ovate with one notch. Intermediate—ovate with two notches. Inside—ovate; scalloped, with one notch.

This description of a newly opened flower was made from a rose grown in a greenhouse, in March, 1940, at Murray Hill, New Jersey:

*Color.*—Outside petal: outside surface—Ox-Blood Red, Plate I; inside surface—Carmine over Spectrum Red, Plate I. Intermediate petal: outside surface — Ox-Blood Red over Carmine, Plate I; inside surface—Carmine over Spectrum Red, Plate I. Inner petal: outside surface—Ox-Blood Red over Carmine, Plate I; inside surface—Carmine over Spectrum Red, Plate I.

This description was made from a rose that was open for three days, in a greenhouse, in March, 1940:

*Color.*—Outside petal: outside surface — Ox-Blood Red toned with Carmine, Plate I; inside surface—Carmine toned with Spectrum Red, Plate I. Inside petal: outside surface—Pomegranate Purple, Plate XII; inside surface—Rose Red, Plate XII, veiled with Carmine, Plate I.

*General color effected.*—Newly opened flower—Carmine on Spectrum Red, Plate I. Three days open—Carmine on Spectrum Red, Plate I.

*Behavior.*—Drop off cleanly; fading Purple.

*Flower longevity.*—On bush in garden, 4 to 5 days in June. Cut roses, grown outdoors. 4 to 5 days in June; cut roses down in greenhouse kept at living room temperatures, 5 to 7 days in March.

*Reproductive organs*

Stamens: Medium number; arranged irregularly about pistils.

Filaments: Medium length; Carmine, Plate I; most with anthers.

Anthers: Medium size; Orange Chrome and Orange Rufous, Plate II; open at various times.

Pollen: Moderate; Light Cadmium, Plate IV.

Pistils: Medium number.

Styles: Uneven, medium length, bunched.

Stigma: Antique Brown, Plate III.

Ovaries: All enclosed in calyx.

Hips: Long with inconspicuous neck pear-shaped; russet; moderately smooth; walls thick, fleshy.

Sepals: Moderately long, curled.

Seeds: Few, medium size.

*Plant*

Foliage:

*Leaves.*—Compound of three, five, seven; moderately abundant; moderately large; moderately leathery.

*Leaflets.*—Ovoid with apex acute; base round; margin simply serrate.

*Color.*—*Mature*: upper surface—Elm Green, Plate XVII; under surface—Bice Green, Plate XVII. *Young*: upper surface—Dark Green; under surface—Light Red.

*Rachis.*—(The supporting stem of the compound leaf) medium heavy. Upper side—Smooth, grooved. Under side—Moderately thorny.

*Stipules.*—Medium length, narrow, with short points, turning out at an angle of less than 45°.

*Disease.*—Subject to mildew and blackspot.

Growth:

*Habit.*—Bushy; upright; much branched.

*Growth.*—Vigorous.

*Canes.*—Medium heavy.

*Main stems.*—Dull; Spinach Green, Plate V. *Thorns*—several; medium length; hooked downward; with broad base. *Prickles*—several; ferruginous, Plate XIV. *Hairs*—none.

*Branches.*—Dull; Cerro-Green, Plate V. *Thorns*—several; short; hooked downward with broad base. *Prickles*—few. *Hairs*—none.

*New Shoots.*—Green. *Thorns*—several; medium length; hooked downward with long, broad base. *Prickles*—few; reddish. *Hairs*—few; Green.

I claim:

A new and distinct variety of hybrid tea rose plant, characterized as to novelty by its habit of growth, abundance of foliage and blooming qualities, together with its excellent form, novel coloring and fragrance, and adaptation for garden decoration purposes, substantially as shown and described.

LYMAN B. CODDINGTON.